United States Patent [19]

Rhodes

[11] 4,305,922

[45] Dec. 15, 1981

[54] LABELING PROTEINS WITH 99M-TC BY LIGAND EXCHANGE

[75] Inventor: Buck A. Rhodes, Albuquerque, N. Mex.

[73] Assignee: University Patents, Inc., Norwalk, Conn.

[21] Appl. No.: 948,439

[22] Filed: Oct. 4, 1978

[51] Int. Cl.$^3$ .................. A61K 29/00; A61K 43/00; G01T 1/00; C07G 7/00
[52] U.S. Cl. ............................ 424/1; 260/112 B; 424/9
[58] Field of Search ..................... 424/1, 9, 1.5; 260/112 B

[56] References Cited

U.S. PATENT DOCUMENTS

| | | | |
|---|---|---|---|
| 3,749,556 | 7/1973 | Barak et al. | 424/1 |
| 3,803,299 | 4/1974 | Novel | 424/1 |
| 3,862,299 | 1/1975 | Bruno et al. | 424/1 |
| 3,902,849 | 9/1975 | Barak et al. | 424/1 |
| 4,001,387 | 1/1977 | Barak et al. | 424/1 |
| 4,042,677 | 8/1977 | Molinski et al. | 424/1 |
| 4,057,617 | 11/1977 | Abramovici et al. | 424/1 |
| 4,094,965 | 6/1978 | Layne et al. | 424/1 |

*Primary Examiner*—Leland A. Sebastian
*Assistant Examiner*—Christine M. Nucker

*Attorney, Agent, or Firm*—Mason, Kolehmainen, Rathburn & Wyss

[57] ABSTRACT

A new method for labeling proteins with 99m-technetium: (1) Start with any volume of technetium (pertechnetate and saline) solution and add 0.1 ml of stannous solution (stannous fluoride-acetate solution) per 15-20 ml of saline. The stannous ions will reduce the pertechnetate to technetium IV. (2) Pour the solution onto a sterile Sephadex G-25 column, The reduced technetium (Tc-IV) will bind to the very top layer of Sephadex. (3) Wash the column with saline solution to remove any free pertechnetate or unusual species of technetium. (4) Add the protein in the minimum volume of water to the top of the Sephadex column. Wait 30 minutes. During this waiting period ligand exchange will occur and the technetium will become bound to the protein, but only to those sites on the protein that form a stronger ligand bond than the Sephadex. This means that the only product that will be formed will be technetium strongly bound to proteins. (5) Wash the labeled protein through the column by adding 1 cc of human serum albumin solution diluted 50/50 with ACD. (6) When this has all soaked into the column, add 5 cc of saline, which means that since the volume of the column is 5 cc there will be 6 cc of eluate. The last (or 6th) cc will contain the Tc-labeled human serum albumin. The impurities will remain on the column.

9 Claims, 1 Drawing Figure

Elution profile of 99mTc-human serum albumin labeled by ligand exchange. The hatched part of the bars represent protein bound radioactivity measured by thin layer chromatography. Non-protein bound radioactivity (99mTc-pertechnetate) is eluted after the 99mTc-labeled protein.

LABELING PROTEINS WITH 99M-TC BY LIGAND EXCHANGE

This invention relates to an improved method of labeling proteins with technetium-99m. More particularly it relates to a procedure for labeling proteins with $^{99m}Tc$ by ligand exchange.

BRIEF DESCRIPTION OF THE INVENTION

In accordance with this invention, a solution of $^{99m}Tc$ ions is passed over or through a bed of particles of a chelating agent. The $^{99m}Tc$ become chelated with the agent and removed from the solution. In this procedure very dilute solutions of $^{99m}Tc$ ions can be used, and the $^{99m}Tc$ ions are collected and concentrated on the particles of chelating agent. Thereafter, the $^{99m}Tc$ ions are removed from the chelating agent by contact with a solution of a protein, such as human serum albumin. The $^{99m}Tc$ ions are preferentially absorbed by the protein through ligand exchange, and they are firmly bonded to the protein molecule.

The preferred chelating agent is polymeric gel known as Sephadex which has a high content of hydroxyl groups in polysaccharide chains. It is strongly hydrophilic and thus swells in water and aqueous solutions. It is produced in the form of minute beads and is generally used as a chromatographic material for separating substances according to molecular size by gel chromatography. In the G-series, Sephadex is available in different particle sizes, varying from as small as 10 microns to as coarse as 300 microns. It is stable in water, salt solutions, organic solvents, alkaline solutions and weakly acidic solutions. In this invention Sephadex G-25 is preferred in the form of particles 100–300 microns in diameter.

Sephadex particles are described in the Flodin U.S. Pat. No. 3,208,994 issued Sept. 28, 1965, the disclosure of which is incorporated herein by reference.

BACKGROUND OF THE INVENTION

Proteins have been labeled with radioactive metals such as technetium-99m to produce radiolabeled materials which can be used as radiotracers and radioscanners in humans. For example, the Dugan U.S. Pat. No. 3,812,245 issued May 21, 1974 describes radiolabeled streptokinase and urokinase labeled with $^{99m}Tc$ and their production by contacting streptokinase or urokinase with an aqueous solution containing $^{99m}Tc$ ions. The $^{99m}Tc$ ions are bonded to the streptokinase or urokinase, probably through hydroxyl groups.

It has been found, however, that the $^{99m}Tc$ ions are not all firmly bonded to the streptokinase or urokinase by the procedure of the Dugan patent, and when the $^{99m}Tc$-labeled materials are injected into the blood stream, to locate thromboembolisms, for example, some of the $^{99m}Tc$ ions become disassociated from the streptokinase or urokinase. These disassociated $^{99m}Tc$ ions are radioactive and are detected in scanning, thus producing anomalous results.

It is an object of this invention to provide a procedure for labeling proteins with $^{99m}Tc$ which results in firmly bonded $^{99m}Tc$ atoms. It is a further object to provide a procedure for labeling proteins with $^{99m}Tc$ by ligand exchange. Another object is to provide new technetium-labeled proteins. These and other objects are apparent from and are achieved in accordance with the following disclosure.

GENERAL DESCRIPTION OF THE INVENTION

I have discovered that proteins can be labeled with technetium-99m by ligand exchange and that the proteins so-labeled contain $^{99m}Tc$ atoms which are firmly bonded and do not disassociate from the protein in aqueous solution. This desirable result is achieved by first contacting an aqueous solution containing $^{99m}Tc$ ions with a chelating agent whereby the $^{99m}Tc$ ions are chelated with hydroxyl groups of the agent and become firmly bonded to the particles. The particles are then washed with saline solution to remove soluble materials. Next the complex containing the chelated $^{99m}Tc$ is contacted wit a solution of protein and the $^{99m}Tc$ ions preferentially migrate from the chelating agent to the protein, becoming firmly bonded to the latter. The $^{99m}Tc$-labeled protein is then separated from the agent by washing and the result is a solution for parenteral administration to subjects for radioscanning. The $^{99m}Tc$ atoms are all firmly bonded to protein and none are in solution as ions which would otherwise complicate or interfere with the scanning.

The step of first bonding the $^{99m}Tc$ ions to a chelating agent and then preferentially transferring the $^{99m}Tc$ ions from the agent to the protein provides a procedure for producing very pure, uniform $^{99m}Tc$-labeled protein in aqueous solution without extraneous metal ions including $^{99m}Tc$ ions. Such aqueous solution is important in radioscanning and in radiotracers.

The chelating agent used in this procedure is insoluble in water and thus inert to proteins. It contains numerous hydroxyl groups about six-membered rings which can form chelates with $^{99m}Tc$ ions. After the technetium ions are chelated with the agent, the resulting chelate is washed with saline (NaCl) solution to remove other undesirable soluble materials, including technetium ions which are not chelated. Then the chelate of technetium and chelating agent is contacted with a solution of protein and there is a ligand exchange of technetium ions between the agent and the protein. After this exchange the protein with the chelated $^{99m}Tc$ attached thereto, being water-soluble, can be washed out of the chelating agent with saline solution and collected. The result is a solution of $^{99m}Tc$-labeled protein suitable for parenteral administration.

DETAILED DESCRIPTION OF THE INVENTION

Figure 1:
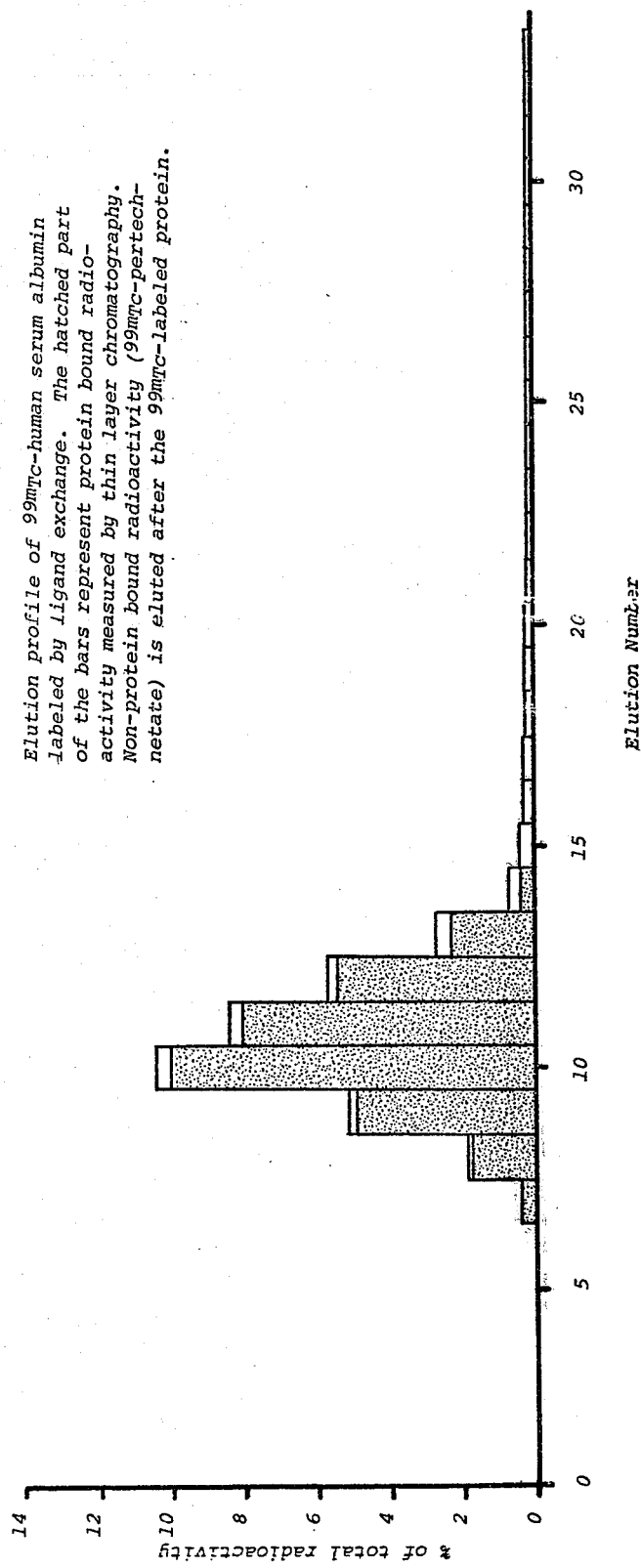
FIG. 1 shows the profile of radioactivity as a function of the elution volume of a Sephadex G-25 column as described in Example 2.

Suitable chetate-forming particles of the type described above are available commercially. One that is preferred is Sephadex G-25, which is a water-insoluble gel of dextran cross-linked with epichlorohydrin, ethylene oxide or propylene oxide, sold by Pharmacia, Inc., Piscataway, N.J., and described in literature of the manufacturer. One form is described in The Merck Index, 9th edition, page 982 (1976). It is available as hydrophilic, water-insoluble, molecular sieve, chromatographic particles (beads).

The source of the technetium-99m ($^{99m}Tc$) preferably is a water-soluble salt such as an alkali or alkaline earth metal pertechnetate. The technetium can be obtained as sodium pertechnetate Tc-99m from a conventional 99Mo/99 mTc generator. Any source of pharmaceutically acceptable technetium-99m may be utilized in the present invention.

In the ligand exchange procedure, a solution of technetium (IV) ions is prepared by mixing a solution of technetium in the form of a pertechnate ($TcO_4{}^-$) in saline solution with a stannous reducing solution, e.g. stannous fluoride-acetate having a pH between about 3 and 5.5. In this procedure, the stannous ions reduce technetium (VII) to technetium (IV). The reduced technetium-99m first is chelated onto the top of a column of Sephadex G-25 (dextran cross-linked gel) by passing the aqueous solution of technetium-99m at a pH between about 5.5 and 7.0 through the column. The column then is washed with saline solution to remove free pertechnate ($TcO_4{}^-$) or unusual species of technetium, thereby leaving the technetium-99m chelated or absorbed or otherwise bound to the Sephadex column. A physiologic solution of protein (e.g., anti-human chorionic gonadotropin; anti-HCG and/or anti-HCG-beta) then is prepared with appropriate buffer so that the resultant solution has a pH between about 6 and 9, preferably between about 7 and 8. Within this pH range, denaturation of anti-HCG or anti-HCG-beta is eliminated or minimized. The protein is then added in a minimum volume of water to the top of the column where the technetium-99m/stannous complex is bound and where it is allowed to stand until the technetium-99m is bound to the protein having stronger bonding sites than the column material. This usually occurs without about 30 minutes. The column then is washed to remove the labeled anti-HCG or anti-HCG-beta. Washing can be effected with a known volume of ACD solution or the like followed by a known volume of saline solution. In this manner, the volume of washing saline solution containing the labeled protein can be determined and the labeled protein can be collected. Impurities in the anti-HCG or anti-HCG-beta will remain on the column or will be eluted at a rate different from that of the labeled, immunologically intact, anti-HCG or anti-HCG-beta.

In forming the products of this invention, a solution of the technetium-99m as the pertechnate is poured onto the column in order to bind the technetium thereon. A physiologically acceptable aqueous solution of the anti-HCG or anti-HCG-beta then is poured onto the column in order to bind the labeled technetium to the anti-HCG or anti-HCG-beta. The labeled protein then is eluted from the column with saline or an otherwise appropriate buffer and is collected from the bottom of the column in a form suitable for intravenous administration to a patient. In an alternative embodiment the eluted labeled protein is passed through a bed of anion-exchange resin in order to remove free pertechnate from the labeled protein, thereby to form a pure labeled anti-HCG or anti-HCG-beta or mixtures thereof, substantially free of radiochemical contamination. If desired, these anion-exchange resins need not be part of the columns utilized for labeling but can comprise a separate bed through which the labeled protein is passed.

The labeled protein is administered by intravenous injection in a pharmaceutically acceptable saline solution, sterile and pyrogen-free. Suitable dosages are usually between about 5 and 30 millicuries, preferably between about 10 and 20 milicuries of technetium-99m for the normal 70 kg patient. The patient then can be scanned by conventional scintigraphy within about 1 hour to about 6 hours after administration of the labeled protein. Tumors are located in those areas showing a high concentration of $^{99m}Tc$-labeled protein.

The following examples illustrate the present invention and are not intended to limit the same.

EXAMPLE 1

Human Chorionic Gonadotropin Labeled with $^{99m}Tc$ By Ligand Method

This example illustrates a ligand exchange process for obtaining the anti-HCG-beta or anti-HCG labeled with $^{99m}Tc$. Anti-HCG or anti-HCG-beta is obtained from Serono Laboratories, Inc., Boston, Mass. Technetium-99m is obtained from New England Nuclear Corporation, Boston, Mass. To 0.1 to 15.0 ml of an aqueous solution of sodium pertechnetate Tc-99m (pH 5 to 7) is added 0.1 ml of aqueous acetate solution containing stannous fluoride, pH 3 to 5.5. The stannous ions reduce the pertechnetate ions to technetium IV. The solution then is poured into a sterile 5 cc column of Sephadex G-25 and then reduced technetium is bound to the very top of the column. The column then is washed with saline solution to remove any free pertechnetate and other unbound species of technetium. A solution of proper ionic strength and pH containing anti-HCG-beta or anti-HCG is added to the top of the column. After about 30 minutes, substantially complete ligand exchange occurs to bind the technetium to anti-HCG or anti-HCG-beta. The column then is washed with ACD (acidified citrate-dextrose) buffer solution. After the albumin solution has soaked completely into the column, 5 cc of saline is added to the column, and the sixth cc of eluate is collected which contains the technetium-99m anti-HCG-beta or anti-HCG.

EXAMPLE 2

Human Serum Albumin Labeled with $^{99m}Tc$ By Ligand Exchange 17 ml of sodium pertechnetate solution, U.S.P., containing approximately 2.5 uCi of radioactive $^{99m}Tc$ was reduced by the addition of 0.1 ml of 1% $SnF_2$ in 0.015 N acetic acid. 1 ml of the reduced $^{99m}Tc$ solution was placed on a 1.5×10 cm Sephadex G25 column that had previously been washed three times with 5 ml of 0.9% saline solution. After 8 minutes 4 ml of 0.9% saline solution was added to the column.

Next 1.0 ml of human serum albumin solution (12.5% normal serum albumin, salt-poor, U.S.P. in an acid citrate, dextrose, ascorbic acid solution) was added to the top of the column and allowed to remain undisturbed for 30 minutes for ligand exchange to occur, i.e., the reduced $^{99m}Tc$ moves from the Sephadex (solid phase) to the albumin (in the liquid phase). To prepare the albumin solution, 2 ml of ascorbic acid (500 mg) was added to 10 ml of ACD Solution (modified) available from Mallinkrodt Nuclear, St. Louis, Mo.; 5 ml of this solution was mixed with 5 ml of 25% normal serum albumin (human), salt-poor, U.S.P. This solution is prepared fresh for each experiment.

After 30 minutes during which ligand exchange occurred, the Sephadex column was eluted with 0.9% saline (NaCl) solution and 1 ml aliquots were collected serially. Each aliquot was analyzed as described below.

Measurement of radioactivity: The $^{99m}Tc$ was determined in each ml of eluate by gamma ray spectrometry. The reference counting standard was a 1 ml aliquot of the reduced $^{99m}Tc$ prepared by the procedure of the first sentence of this example. Percent of total radioactivity per ml of eluate was determined.

Protein was detected in each ml of eluate by addition of 1-2 drops of 20% trichloracetic acid to each tube. Protein is indicated by the presence of a milky precipitate.

The results are given in FIG. 1 which shows the profile of radioactivity as a function of elution volume (in ml). 50.35% of the radioactivity appeared in those tubes containing the protein.

Control studies were conducted omitting the reducing agent and the $^{99m}$Tc was not bound to the Sephadex column. The protein in the eluate did not correspond to the peak of radioactivity in the eluate. The radioactivity elution pattern was that of pertechnetate.

Another control study omitted the human serum albumin. In this case the $^{99m}$Tc remained bound to the Sephadex column. Varying the amounts of labeling solution and the composition of the eluting solutions causes changes in the amount of radioactivity eluted with the protein fraction. Analysis of the protein fraction of the eluate by thin layer chromatography shows that the $^{99m}$Tc in the solution is protein-bound.

From these studies it was determined that:

$^{99m}$Tc is labeled to human serum albumin by ligand exchange of the reduced $^{99m}$Tc from the solid phase to the protein in the aqueous phase.

40 to 70% of the $^{99m}$Tc becomes bound to the albumin.

The Sephadex column chromatography separates the $^{99m}$Tc-pertechnetate and reduced hydrolyzed technetium. The pertechnetate is eluted after the protein while the reduced hydrolyzed technetium remains bound to the Sephadex.

The aqueous solution of $^{99m}$Tc-labeled human serum albumin so produced can be used for scanning human organs and tissues, particularly for placental and cardiac scanning.

EXAMPLE 3

Human Fibrinogen Labeled With $^{99m}$Tc By Ligand Exchange 16 ml of sodium pertechnetate (tc-99m) solution, U.S.P. containing approximately 3.5 uCi of radioactivity was reduced with 0.1 cc of 1.0% SnF$_2$ solution in 0.015 acetic acid. 1 ml of the reduced $^{99m}$Tc solution was added to a 1.5 by 10 cm column of Sephadex G-25 that has previously been washed three times with 5 ml of 0.9% saline. Next 4 ml of 0.9% saline solution was added to the column. $^{125}$I-labeled fibrinogen (1 ml) is mixed with 1 ml of the acid citrate-dextrose-ascorbic acid solution described in Example 1, and 0.2 ml of the resulting solution was added to the top of the column. The column was then eluted with 0.9% saline solution and 1 ml aliquots were collected serially.

The a liquots were analyzed as follows:

Measurement of radioactivity: $^{125}$I and $^{99m}$Tc were measured simultaneously by gamma ray spectrometry. Reference counting standards were separate samples of the $^{125}$I-fibrinogen and the reduced $^{99m}$Tc solution.

Clottable protein: 0.05 ml of thrombin, topical (bovine origin) such as that sold by Parke, Davis and Co., Detroit, Mich., was added to each eluate tube after 0.1 ml of serum plasma. This produced clots which were washed three times with 0.9% saline solution. The $^{125}$I and $^{99m}$Tc radioactivities were then remeasured by gamma ray spectrometry. Table 1 shows recoveries of clottable radioactivities.

|  | % Clottable Radioactivity | |
| --- | --- | --- |
|  | $^{99m}$Tc | $^{125}$I |
| Trial 1 | 47.8 | 90.5 |
| Trial 2 | 58.8 | 95.3 |

The elution profile of $^{99m}$Tc was the same as that for $^{125}$I.

The recovery of the $^{125}$I was approximately 50%.

This example demonstrates that $^{99m}$Tc can be exchange-labeled onto human fibrinogen, and that approximately 50% of the $^{99m}$Tc-labeled human fibrinogen solution so produced can be used in scanning human organs and tissues.

EXAMPLE 4

Ligand Exchange Labeling of Human Serum Albumin

Materials:
1. 16 ml of sodium pertechnetate-Tc-99 m, containing 3.5 uCi to 350 mCi of radioactivity.
2. 10 ml of A-C-D Solution (modified), Mallinckrodt, Inc., St. Louis, Miss., to which 2 ml of ascorbic acid, Injection, U.S.P. The Vitarine Co., Inc., New York, N.Y. (500 mg. in 2 ml) is added.
3. Sterile, 1×10 cm chromatographic column containing Sephadex G-25 (Pharmacia Fine Chemicals, Piscataway, N.J.).
4. 0.9% sodium chloride (non-preservative, nonbacteriostatic) solution.
5. 25% human serum albumin (salt-poor). This is diluted 1:1 with the modified A-C-D ascorbic acid solution.
6. Stannous fluoride (SnF$_2$), Sigma Chemical Co., St. Louis, Mo., 1% in 0.16 molar hydrochloric acid.

Procedure:
1. Wash the Sephadex column 3 times with 7 ml volumes of 0.9% sodium chloride.
2. Add 0.1 ml of SnF$_2$ solution to each 10 ml of sodium pertechnetate solution, mix and pour onto the Sephadex column, allow to drain.
3. Wash column with 4 ml of 0.9% saline, allow to drain.
4. Add 0.2 ml of human serum albumin: A-C-D: Ascorbic acid solution to the top of the column, allow to stand 5 minutes to permit ligand exchange labeling of the protein with the Tc-99m.
5. Elute the column with A-C-D; ascorbic acid collecting the sixth through fourteenth ml of eluant which contains the radiochemically purified product, Tc-99m labeled human serum albumin.

I claim:

1. Method of labeling protein with technetium-99 m without denaturing the protein, which comprises forming a complex of technetium-99m IV with a water-insoluble chelating agent by contacting said chelating agent with a solution of technetium-99m IV, washing said complex to remove undesired ions, contacting said complex with an aqueous protein solution and separating the aqueous solution of protein labeled with technetium-99m IV from the complex.

2. Method of claim 1 wherein the protein is human serum albumin.

3. Method of claim 1 wherein the protein is human fibrinogen.

4. Method of claim 1 wherein the chelating agent is a polymer of dextran cross-linked with epichlorohydrin, ethylene oxide or propylene oxide.

5. Method of claim 4 wherein the time of contact of the complex with aqueous protein solution is from about 5 to about 30 minutes.

6. $^{99m}$Tc-labeled human fibrinogen wherein the Tc has a valence of 4.

7. A water-insoluble complex of $^{99m}$Tc IV and a polymer of dextran cross-linked with epichlorohydrin, ethylene oxide or propylene oxide.

8. $^{99m}$Tc-labeled anti-human chorionic gonadotropin wherein the Tc has a valence of 4.

9. $^{99m}$Tc-labeled human anti-chorionic gonadotropin-beta wherein the Tc has a valence of 4.

* * * * *